(12) United States Patent
Xu et al.

(10) Patent No.: US 12,285,528 B2
(45) Date of Patent: Apr. 29, 2025

(54) INJECTABLE FORMULATIONS OF ANESTHETICS FOR ANY PATHOLOGICAL PAIN

(71) Applicants: New Jersey Institute of Technology, Newark, NJ (US); Rutgers, The State University of New Jersey, New Brunswick, NJ (US)

(72) Inventors: Xiaoyang Xu, Livingston, NJ (US); Yuanxiang Tao, Newark, NJ (US)

(73) Assignees: New Jersey institute of Technology, Newark, NJ (US); Rutgers, The State University of New Jersey, New Brunswick, NJ (US)

( * ) Notice: Subject to any disclaimer, the term of this patent is extended or adjusted under 35 U.S.C. 154(b) by 584 days.

(21) Appl. No.: 17/289,601

(22) PCT Filed: Oct. 31, 2019

(86) PCT No.: PCT/US2019/059043
§ 371 (c)(1),
(2) Date: Apr. 28, 2021

(87) PCT Pub. No.: WO2020/092698
PCT Pub. Date: May 7, 2020

(65) Prior Publication Data
US 2021/0369628 A1    Dec. 2, 2021

Related U.S. Application Data

(60) Provisional application No. 62/753,997, filed on Nov. 1, 2018.

(51) Int. Cl.
| | | |
|---|---|---|
| *A61K 9/50* | (2006.01) | |
| *A61K 9/00* | (2006.01) | |
| *A61K 31/135* | (2006.01) | |
| *A61K 31/137* | (2006.01) | |
| *A61K 31/167* | (2006.01) | |
| *A61K 31/381* | (2006.01) | |
| *A61K 31/4168* | (2006.01) | |
| *A61K 31/4174* | (2006.01) | |
| *A61K 31/445* | (2006.01) | |
| *A61K 31/46* | (2006.01) | |
| *A61K 31/485* | (2006.01) | |
| *A61K 31/5517* | (2006.01) | |
| *A61K 31/573* | (2006.01) | |
| *A61K 33/00* | (2006.01) | |
| *A61P 23/02* | (2006.01) | |

(52) U.S. Cl.
CPC .......... *A61K 9/5031* (2013.01); *A61K 9/0019* (2013.01); *A61K 31/135* (2013.01); *A61K 31/137* (2013.01); *A61K 31/167* (2013.01); *A61K 31/381* (2013.01); *A61K 31/4168* (2013.01); *A61K 31/4174* (2013.01); *A61K 31/445* (2013.01); *A61K 31/46* (2013.01); *A61K 31/485* (2013.01); *A61K 31/5517* (2013.01); *A61K 31/573* (2013.01); *A61K 33/00* (2013.01); *A61P 23/02* (2018.01)

(58) Field of Classification Search
None
See application file for complete search history.

(56) References Cited

U.S. PATENT DOCUMENTS

| | | | |
|---|---|---|---|
| 9,943,466 B1 | 4/2018 | Johnson et al. | |
| 2004/0115254 A1* | 6/2004 | Niedzinski | A61K 9/1272 514/44 R |
| 2007/0098800 A1 | 5/2007 | Giroux et al. | |
| 2009/0202436 A1 | 8/2009 | Hobot et al. | |
| 2015/0182512 A1 | 7/2015 | King | |
| 2015/0250724 A1 | 9/2015 | Yamashita et al. | |

FOREIGN PATENT DOCUMENTS

WO    WO 99/36071 A1    7/1999

OTHER PUBLICATIONS

Ni et al. (Drug Design, Development and Therapy 2016:10 2499-2506).*
International Search Report and Written Opinion in corresponding International Application No. PCT/US2019/059043, mailed Jan. 24, 2020.
International Preliminary Report on Patentability in corresponding International Application No. PCT/US2019/059043, issued Apr. 27, 2021.

* cited by examiner

*Primary Examiner* — Bong-Sook Baek
(74) *Attorney, Agent, or Firm* — Leason Ellis LLP

(57) ABSTRACT

An injectable formulation for a sustained-release of a local anesthetic is provided. The formulation comprises a pharmaceutically effective amount of a local anesthetic encapsulated into polymeric particles having a diameter from about 1 μm to about 4 μm. Such formulation prolongs analgesic effect, decreases toxicity, and allows loading larger doses, and at the same time is injectable directly at a patient's body site of the interest without generating a surgical wound. Methods of use and preparation are also provided.

19 Claims, 8 Drawing Sheets

INJECTABLE FORMULATIONS OF ANESTHETICS FOR ANY PATHOLOGICAL PAIN

CROSS-REFERENCE TO RELATED PATENT APPLICATIONS

This application is a U.S. National Phase Application under 35 U.S.C. § 371 of International Patent Application No. PCT/US2019/059043, filed Oct. 31, 2019, and claims the benefit of priority under 35 U.S.C. Section 119(e) of U.S. Application Ser. No. 62/753,997, filed Nov. 1, 2018. The International Application was published on May 7, 2020 as International Publication No. WO 2020/092698 A1.

TECHNICAL FIELD

The present disclosure is directed to injectable formulations for delivering local anesthetic agents, methods of preparing, and uses thereof to provide a long-lasting analgesic effect on pain, particularly, on pathological pain such as incisional pain and neuropathic pain.

BACKGROUND

Despite great efforts put into research and management for pain, during the past decades, pathological pain control remains a challenge in the patients. Effective control and management of pathological pain are among the primary concerns to the patients and medical care providers. Inadequate treatment of pathological pain continues to be an important clinical problem, leading to not only adverse outcomes during the immediate pathological period but also an increased risk for persistent (or chronic) pathological pain.

In order to provide local or regional blockade for pain, clinicians normally use peripheral nerve blocks for local anesthetics through catheter infusion or syringe injection to a site where the pain is to be blocked. Local anesthetics (LAs), such as lidocaine, bupivacaine, ropivacaine, and their analogs, usually have low molecular weight, and therefore present fast systemic absorption. As a consequence, the duration of their analgesic effect is short. Anesthetics when applied subcutaneously rarely last longer than eight hours. Furthermore, the risk of systemic toxicity precludes the use of high bolus doses. Pathological pain lasts from several days to several months, and in some cases, even more than one year, and therefore requires repeated administration of LAs, which potentially causes irreversible damage to nerves or surrounding tissues due to fluctuations in concentration, or requires continuous infusion through an implanted catheter, which requires the surgery for the catheter implantation. As such, there is a compelling need for formulations providing a prolonged analgesic effect.

One avenue of investigation has focused on encapsulating LAs within nanocarriers to prolong anesthetic effect, decrease toxicity, and allow larger LA loading dose. Various nano-sized drug delivery systems for LAs, including by using liposomes, hydrogels, polymeric nanoparticles, solid lipid nanoparticles, and nanostructured lipid carriers, have been studied. However, toxicity, tissue reaction to such formulations, and efficacy have been problematic. Conventional LAs are intrinsically myotoxic. They are also myotoxic when released from a wide range of delivery systems, even when the delivery systems themselves are minimally toxic. Conventional LAs are also neurotoxic. The presence of particles themselves enhances local anesthetic myotoxicity in vivo, and can cause inflammatory responses at the nerve that may considerably outlast the duration of blockade. Nano-formulation can help extending the duration of the release. However, due to its fast diffusion rate, it still cannot meet the need for prolonged duration of analgesic effect.

Meanwhile, sustained release strategy has been explored by using polymeric particles in a size of about 5 µm to 500 µm in diameter as carriers. However, generally such formulations are not injectable, but have to be placed inside of the body through surgery, and therefore their clinical application in a non-invasive or minim-invasive administration method is limited.

In the past three decades, biodegradable materials particularly biodegradable polymers have been extensively studied as biomaterials for tissue engineering and drug delivery. Poly lactic-co-glycolic acid (PLGA) has been among the most attractive biodegradable polymers used to fabricate devices for controlled delivery of small drug molecules, therapeutic proteins, nucleic acid based therapeutics and other macromolecules. PLGA is biocompatible and can degrade in the body via hydrolysis of its ester linkages in the presence of water. Importantly, the by-products of the hydrolysis process are its original monomers, lactic acid and glycolic acid, which can be further eliminated by the normal metabolic pathways under normal physiological conditions. Additionally, PLGA exhibits a wide range of erosion time and tunable mechanical properties by adjusting the ratio of lactide to glycolide used for the polymerization.

Accordingly, there is a continuing need for an injectable sustained-release formulation of a local anesthetic, preferably biodegradable, for providing a long-lasting analgesic effect on pain, particularly, on pathological pain such as incisional pain and neuropathic pain, in a non-invasive or minim-invasive manner of administration.

SUMMARY OF THE INVENTION

In accordance with embodiments of the present disclosure, an injectable formulation for a sustained-release of a local anesthetic is provided. Such formulation prolongs analgesic effect, decreases toxicity, and allows larger loading dose, and at the same time is injectable directly at a patient's body site of the interest without generating a surgical wound. The local anesthetic may be sustained-released up to about 14 days.

In one embodiment, a pharmaceutically effective amount of local anesthetic may be encapsulated into polymeric particles having a diameter of about 1 µm to about 4 µm, preferably about 1 µm to about 2 µm. The local anesthetic includes, but is not limited to, articaine, bupivacaine, dibucaine, etidocaine, levobupivacaine, lidocaine, mepivacaine, prilocaine, ropivacaine, trimecaine, benzocaine, chloroprocaine, cocaine, cyclomethycaine, dimethocaine, piperocaine, propoxycaine, procaine, proparacaine, and tetracaine, mixtures thereof, and pharmaceutically acceptable salts thereof, and others well known in the art, preferably ropivacaine or pharmaceutically acceptable salts thereof. The local anesthetic may be incorporated into the polymer particles in a percent loading of about 0.1% to about 90% by weight, preferably about 1% to about 75% by weight, more preferably about 5% to about 25% by weight. The concentration of the local anesthetic loaded polymer particles in the sustained-release formulation may be up to about 0.25%. The polymeric particles used in the formulation may be any biocompatible polymer known in the art, including co-polymers of hydroxy acids such as lactic acid and glycolic acid, polyglycolic acid, polylactic acid, polyanhydrides, polyorthoesters, polycaprolactones, polyphosphazenes, polysaccharides, proteinaceous polymers, soluble derivatives of polysaccharides, soluble derivatives of proteinaceous polymers, polypeptides, polyesters, polyorthoesters, and mixtures thereof, preferably a biodegradable polymer such as a copolymer of lactic acid and glycolic acid (PLGA). The concentration of the polymeric particles in the formulation may be about 160 to about 200 mg/mL.

In another embodiment of the present disclosure, a method of preparing an injectable formulation for a sustained-release of a local anesthetic is provided.

In one embodiment, the local anesthetic loaded microparticles may be prepared utilizing a solvent evaporation technique, which involves a water in oil in water (w/o/w) double emulsion. An effective amount of the local anesthetic loaded microparticles may be incorporated into a pharmaceutically acceptable vehicle to obtain a solution or suspension for injection.

In another embodiment of the present disclosure, a method of using an injectable sustained-release formulation of a local anesthetic in managing a patient's pain is provided.

In one embodiment, the formulation may be injected to the body site where the local anesthetic is released, without generating a surgical wound. The local anesthetic may be sustained-released up to about 14 days, preferably up to about 6 days. The formulation may be used for the management of various forms of pain, including pathological pain such as incisional pain and neuropathic pain, and chronic pain such as the pain associated with various types of cancer.

In another embodiment of the present disclosure, the use of an injectable sustained-release formulation of a local anesthetic encapsulated into a plurality of polymeric particles in a method for providing sustained pain relief at a site in a patient is provided. The local anesthetic has a loading of 1% to 90% by weight into the plurality of polymeric particles. The local anesthetic is released in a controlled release of 1 to 30 mg of local anesthetic per hour at the release site for a time period ranging from 4 hours to 14 days.

Any combination and/or permutation of the embodiments are envisioned. Other objects and features will become apparent from the following detailed description considered in conjunction with the accompanying drawings. It is to be understood, however, that the drawings are designed as an illustration only and not as a definition of the limits of the present disclosure.

BRIEF DESCRIPTION OF THE DRAWINGS

These and other features, aspects, and advantages of the present disclosure will become better understood with regard to the following description, appended claims, and accompanying drawings in which:

FIG. 5A depicts representative Western blots. FIG. 5B depicts statistical summary of the densitometric analysis.

DETAILED DESCRIPTION

Figure 1:
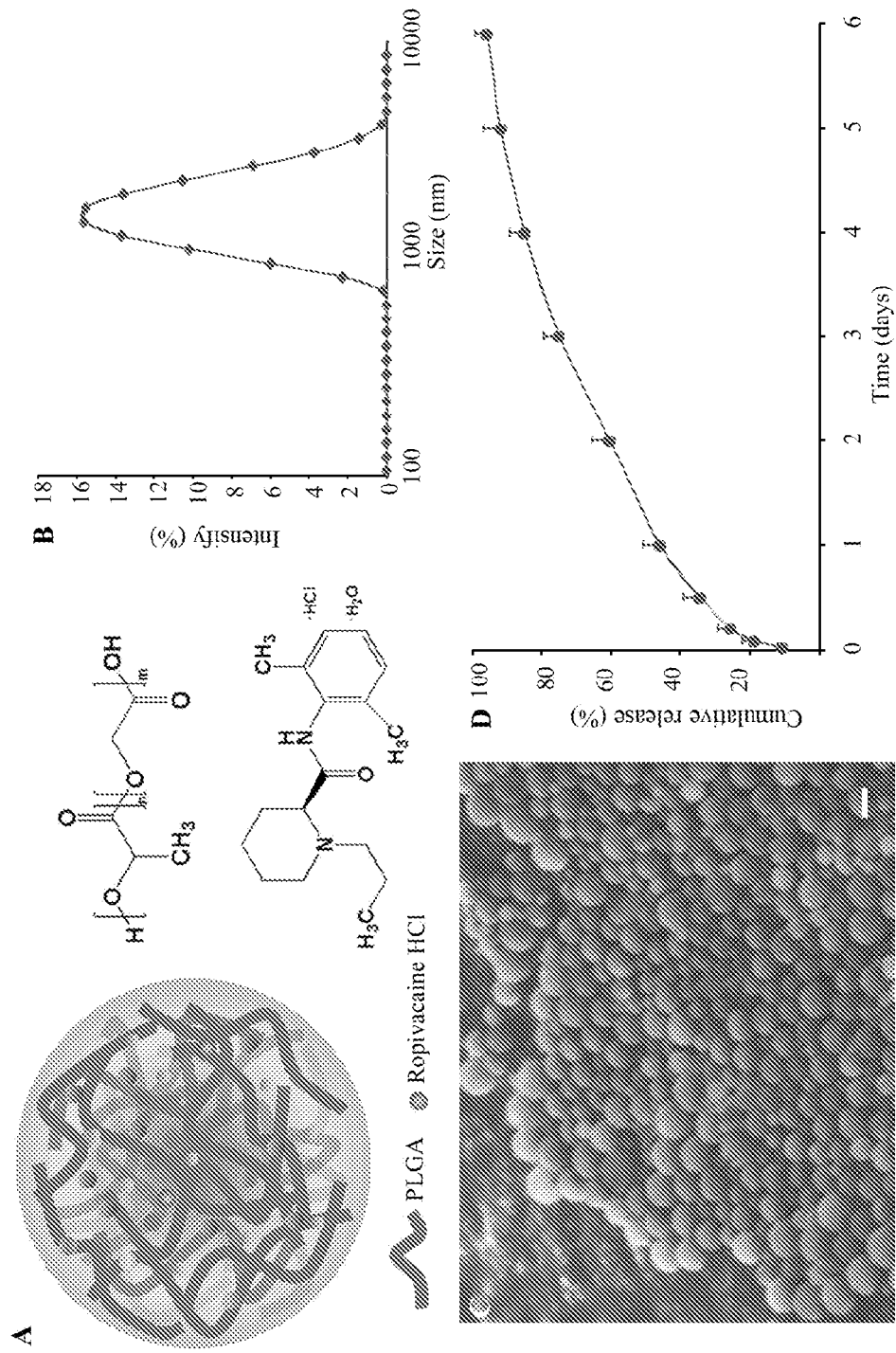
FIG. 1A depicts the structure model of RVC·HCl microparticles.
FIG. 1B depicts the size distribution of PLGA microparticles containing RVC·HCl by dynamic light scattering.
FIG. 1C depicts the representative SEM image of the RVC·HCl microparticles.
FIG. 1D depicts the in vitro release profile of RVC·HCl from PLGA microparticles.

Before describing at least one embodiment of the disclosure in detail, it is to be understood that the present disclosure is not limited in its application to the details set forth in the following description or exemplified by the examples. Aspects of the disclosure are capable of other embodiments or of being practiced or carried out in various ways. Also, it is to be understood that the phrasing and terminology employed herein is for the purpose of description and should not be regarded as limiting.

The present disclosure provides an injectable formulation for a sustained-release of a local anesthetic. The formulation comprises a pharmaceutically effective amount of a local anesthetic encapsulated into polymeric particles having a diameter from about 1 μm to about 4 μm. Such formulation prolongs analgesic effect, decreases toxicity, and allows larger loading dose, and at the same time is injectable directly at a patient's body site of the interest without generating a surgical wound.

As used herein, the term "patient" refers to any animal that is to be treated with the formulations and/or by the methods herein disclosed. Preferably, the term refers to a mammal such as a human.

As used herein, the term "local anesthetic" refers to any drug or mixture of drugs that provides local numbness and/or analgesia. Examples of local anesthetics which can be used include articaine, bupivacaine, dibucaine, etidocaine, levobupivacaine, lidocaine, mepivacaine, prilocaine, ropivacaine, trimecaine, benzocaine, chloroprocaine, cocaine, cyclomethycaine, dimethocaine, piperocaine, propoxycaine, procaine, proparacaine, and tetracaine, and mixtures thereof and any other art-known pharmaceutically acceptable local anesthetics. The local anesthetic can be in the form of a free base or a pharmaceutically acceptable salt, for example, hydrochloride, hydrobromide, acetate, citrate, carbonate or sulfate salt. Compared to the free base form, the hydrochloride salt displays longer and denser nerve block, more release from polymer matrices, and slower clearance from the targeted nerve area. Local anesthetics typically administered systematically may also be used in those cases where the means of administration results only in a local effect, rather than systemic.

Preferably, the local anesthetic may be ropivacaine. Ropivacaine, belonging to the class of amino-amides, is one of the safest LAs in the market, and widely used in the management of pain. Compared to other clinically available LAs, ropivacaine has a relatively long-term effect, and lower cardiovascular and/or systematic toxicity. At low concentration, it may also provide separated sensor and motor block. Commercial ropivacaine hydrochloride (Naropin®) injection is available in single dose containers in 2 (0.2%), 5 (0.5%), 7.5 (0.75%) and 10 mg/mL (1%) concentrations.

As used herein, the term "sustained-release" or "controlled-release" generally refers to using suitable pharmaceutically acceptable carriers to control the release of an active agent or drug incorporated therein, typically to slow the release of the active agent or drug in order to prevent immediate release. Such controlled release formulations or compositions are used herein to prolong or sustain the release of an active agent or drug incorporated, e.g., a local anesthetic. Thus, the terms "sustained-release" and "controlled-release" are generally used interchangeably throughout the present disclosure unless otherwise indicated.

The local anesthetic may be encapsulated into polymeric particles. The loading amount of the local anesthetic depends on the type of the local anesthetic, the type and shape of the polymer used, and the need of the patient in managing pain. The local anesthetic may be incorporated into the polymer particles in a percent loading of about 0.1% to about 90% by weight, preferably about 1% to about 75% by weight, more preferably about 5% to about 25% by weight.

Polymers that are pharmaceutically acceptable, or biocompatible may be utilized in the present sustained-release formulations. Such polymers may include, but are not limited to, co-polymers of hydroxy acids such as lactic acid and glycolic acid—poly(lactic-co-glycolic acid)(PLGA), poly (glycolic acid)(PGA), poly(lactic acid)(PLA), polyanhydrides, polyorthoesters, polycaprolactones, polyphosphazenes, polysaccharides, proteinaceous polymers, soluble derivatives of polysaccharides, soluble derivatives of proteinaceous polymers, polypeptides, polyesters, and polyorthoesters. These polymers have low toxicity and virtually complete biodegradability. The polymeric material used in the present disclosure may have a molecular weight from about 5,000 to about 200,000.

Preferred polymers used herein may be co-polymers of lactic acid and glycolic acid, poly(lactic-co-glycolic acid) (PLGA), wherein the weight ratio of lactic acid to glycolic acid is no more than 4:1 (i.e., 80% or less lactic acid to 20% or more glycolic acid by weight), preferably 1:1. Various PLGAs in a wide range of molecular weights and ratios of lactic acid to glycolic acid are commercially available.

The polymers utilized in the present disclosure may be prepared by the methods known to those skilled in the art. For example, PLGA may be prepared by the condensation of lactic acid and glycolic acid in the presence of a readily removable polymerization catalyst. Such catalysts include strong acid ion-exchange resins in the form of beads or similarly hard structures that are easily removed by filtration or similar techniques.

In one embodiment, the local anesthetic may be encapsulated into polymeric particles as microparticles, microspheres or microcapsules. The terms "microparticles," "microspheres" and "microcapsules" are generally used interchangeably throughout the present disclosure unless otherwise indicated.

The size of the particles may range from about 1 μm to about 4 μm, preferably about 1 μm to about 2 μm, in diameter. In some embodiments, the microparticles may have a diameter from about 1.5 μm to about 4 μm, or from about 2 μm to about 4 μm. If the size of the particles is below 1 μm, the diffusion becomes too fast. On the other hand, if the size of the particles is above 4 μm, the formulation becomes not injectable, but has to be placed inside of the body through surgery. In particular, the size of the particles may be required to be even less than 4 µm to be injectable when the concentration of the drug in the formulation gets larger.

The present injectable sustained-release microparticles may be prepared by methods including, but not limited to, solvent evaporation, phase separation, and fluidized bed coating.

In one embodiment, the local anesthetic loaded microparticles may be prepared utilizing a solvent evaporation technique, which involves a water in oil in water (w/o/w) double emulsion. A polymer material is first dissolved in a solvent such as dichloromethane (DCM). A solution of a local anesthetic is then prepared in a solvent such as polyvinyl alcohol (PVA) in deionized (DI) water. The solution of the local anesthetic is later mixed with the polymer solution using a probe sonicator (Q700 Sonicator, Qsonica, Llc, USA) for about 5 seconds to 5 minutes at 30% amplitude to form the first emulsion. This emulsion is then rapidly added to PVA solution by stirring at 10,000 rpm for about 5 seconds to 5 minutes using a homogenizer (Bio-Gen PRO200. Pro Scientific) to form the second emulsion. The mixture is stirred overnight during which time the DCM solvent is evaporated. The particles are collected by washing 3 times with DI water using a centrifugal filter device (Amicon® Ultra 15 mL Centrifugal Filter. Millipore).

In one embodiment, ropivacaine hydrochloride-loaded PLGA microparticles may be prepared by the above method.

The encapsulation efficiency (EE) of the microparticles prepared by the present methods may be at least about 80%, preferably 100%. The drug loading capacity (DLC) of the microparicles prepared by the present methods may be about 10 to about 30%, preferably about 10 to about 20%. EE and DLC are defined as follows, respectively:

EE (%)=(weight of local anesthetic loaded into microparticles)/(weight of local anesthetic in the system)×100%

DLC (%)=(weight of entrapped local anesthetic/ weight of all materials in the system)×100%

The microparticles used in the present injection formulation provide a sustained action in the localized area to be treated. The formulation comprising such microparticles may have sustained release of the local anesthetic up to about six days in vitro, and up to about two weeks in vivo.

In one embodiment, the present injectable sustained-release formulation may further include a bioadhesive polymer such as pectins (polygalacturonic acid), mucopolysaccharides (hyaluronic acid, mucin), and non-toxic lectins.

An effective amount of the microparticles wherein a local anesthetic is encapsulated may be incorporated into a pharmaceutically acceptable vehicle to obtain a solution or suspension for injection. Such vehicles include, but are not limited to, isotonic saline, buffered (such as phosphate buffered saline (PBS)) or unbuffered and the like, and may optionally include any other art known ingredients or agents, e.g., colorants, preservatives, antibiotics, epinephrine and the like.

A formulation for local anesthesia of the present disclosure can be provided as a composition for injection in a form of an aqueous solution containing local anesthetic encapsulated microparticles described above and one or more optional pharmaceutically acceptable additives, which are known for those skilled in the art. The additives include, but are not limited to, epinephrine, clonidine, dexmedetomidine, buprenorphine, dexamethasone, tramadol, sodium bicarbonate, and midazolam. The amount of the additive added in the formulation of local anesthesia is known to those skilled artisans.

The final reconstituted product viscosity may be in a range suitable for the injection. In certain instances, the final reconstituted product viscosity may be, e.g., about 35 cps. Administration may be via the subcutaneous or intramuscular route.

The dosage of the present sustained-release formulation is dependent upon the kind and amount of the local anesthetic to be administered, the recipient animal, and the objectives of the treatment. The formulation may include from about 0.5 to about 2 mg/kg body weight of the local anesthetic. Since the formulations of the present invention are controlled release, it is contemplated that formulations may include much more than usual immediate release doses, e.g., as much as about 450 mg/kg of the local anesthetic or more. The concentration of the local anesthetic in the sustained-release formulation may be up to about 20 mg/mL.

The effective dose of a local anesthetic can range from about 1 to about 50 mg of a local anesthetic injected at each site where the release of a local anesthetic agent is desired. In certain preferred embodiments, the dose of a local anesthetic in the controlled release dosage form of the invention is sufficient to provide a controlled release of about 1 to about 30 mg of local anesthetic per hour at the release site for the desired duration of anesthesia, e.g., a time period ranging from up to about 4 hours to about 14 days, from up to about 6 hours to about 6 days, or from up to about 12 hours to about 4 days.

The amount of local anesthetic released per day increases proportionately with the percentage of local anesthetic incorporated into the formulation. In one preferred embodiment, polymer matrices or other formulations comprising from about 70% to about 90% by weight, of local anesthetic, are utilized, although it is possible to incorporate substantially more drug, depending on the drug, the method used for making and loading the formulation, and the polymer.

Examples

The following examples are for the purpose of illustration only and are not intended to limit the scope of the invention as defined in the claims hereinafter.

Materials

Poly (lactide-coglycolide) (PLGA, lactic acid:glycolic acid=50:50, carboxylate end group, inherent viscosity range: 0.55~0.75 dL/g) was purchased from Absorbable Polymers International. Polyvinyl alcohol (PVA, 87~89% hydrolyzed, MW 13.000~23,000), dichloromethane (DCM) and Ropivacaine hydrochloride (RVC·HCl) were purchased from Sigma-Aldrich (St. Louis, MO).

Preparation of RVC·HCl-Loaded PLGA Microparticles

RVC·HCl-loaded PLGA microparticles (abbreviated as RVC·HCl microparticles) were prepared utilizing a solvent evaporation technique which involves a water in oil in water (w/o/w) double emulsion. 100 mg of PLGA was dissolved in 5 mL of DCM. A solution of RVC·HCl at a concentration of 20 mg/mL was prepared in 0.5% (w/v) PVA in deionized (DI) water. 1 mL of the RVC·HCl solution was mixed with PLGA/DCM solution using a probe sonicator (Q700 Sonicator, Qsonica, Llc, USA) for 30 seconds at 30% amplitude to form the first emulsion. This emulsion was then rapidly added to 20 mL of 0.5% (w/v) PVA solution by stirring at 10,000 rpm for 30 s using a homogenizer (Bio-Gen PRO200, Pro Scientific) to form the second emulsion. The mixture was stirred overnight during which time the DCM solvent was evaporated. The particles were collected by washing 3 times with DI water using a centrifugal filter device (Amicon® Ultra 15 mL Centrifugal Filter, Millipore).

RVC·HCl Loading on PLGA Microparticles

To determine the encapsulation efficiency (EE) and drug loading capacity (DLC) of RVC·HCl, 10 mg samples of RVC·HCl microparticles were dissolved in 0.2 mL acetonitrile and 0.8 mL DI water. This mixture was agitated using a vortex mixer and centrifuged at 13.000 rpm for 5 min to remove PLGA precipitates. The RVC·HCl content in the supernatant was analyzed by High-Pressure Liquid Chromatography (HPLC) (Agilent 1200 series, USA) with a Agilent Eclipse XDB-C18 column (150 mm×4.6 mm, 5 µm) using a mobile phase consisting of acetonitrile/water (20:80) containing 0.1% trifluoroacetic acid and UV detection at 260 nm. EE and DLC of RVC·HCl microparticles were calculated according to the following formula:

EE (%)=(weight of RVC·HCl loaded into PLGA microparticles)/(weight of RVC·HCl in the system)×100%

DLC (%)=(weight of entrapped RVC·HCl/weight of all materials in the system)×100%

Microparticle Size and Surface Morphology Analysis

Microparticle size and zeta potentials were measured using dynamic light scattering technique (DLS) on Zetasizer Nano ZS (Malvern, Southborough, MA). The particles were suspended in deionized water at a concentration of 1 mg/mL. The mean diameter of the hydrodynamic volume size was confirmed by cumulative analysis. The zeta potential was also measured based on the electrophoretic mobility of the microparticles in aqueous solution, which was confirmed with folded capillary cells. Microparticle morphology was assessed by Scanning Electron Microscopy (SEM, LEO 1530 VP). Air-dried microparticles were placed on adhesive carbon tabs mounted on SEM specimen stubs. The specimen stubs were coated with ~5 nm of carbon before examination in the SEM operated.

In-Vitro Drug Release Study

Drug release tests were carried out at constant body temperature (37° C.). RVC·HCl loaded microparticles (10 mg) were added to 1 mL of 10 mM phosphate-buffered saline (PBS) and incubated at 37° C. by shaking in a Thermomixer (Eppendorf, Germany) at 300 rpm. At predetermined time intervals, the sample was centrifuged at 2000 rpm for 3 min. The supernatant was collected and the medium was replaced with 1 mL of fresh PBS. The amount of RVC·HCl released into each medium was quantified by HPLC analysis. All experiments were performed in triplicate.

Particle Size—Injectability Study

RVC·HCl-loaded PLGA microparticles with different particle sizes were prepared using the method described above. Injectability was studied by using different concentration of the RVC·HCl-loaded PLGA microparticles.

Animal Preparation

Male and female Sprague-Dawley rats weighing 200-250 g were obtained from Charles River Laboratories (Wilmington, MA). All rats were housed in an animal facility that was kept in a standard 12-h light/dark cycle, with standard laboratory water and food pellets available ad libitum. Animal experiments were conducted with the approval of the Animal Care and Use Committee at Rutgers-New Jersey Medical School and were consistent with the ethical guidelines of the US National Institutes of Health and the International Association for the Study of Pain. All efforts were made to minimize animal suffering and to reduce the number of animals used. To minimize intra- and inter-individual variability of behavioral outcome measures, animals were trained for 1-2 days before behavioral testing was performed. The experimenters were blinded to treatment condition during behavioral testing.

Incisional Pain Model

The incisional surgery was carried out with minor modification as described in T. J. Brennan, et al., Characterization of a rat model of incisional pain, Pain, 64 (1996) 493-501. Rats were anesthetized with 2% isoflurane delivered via a nose cone. The plantar aspect of the left hindpaw was prepared in a sterile manner with a 10% povidone-iodine solution. A 1-cm longitudinal incision was made with a number 11 blade, through skin and fascia of the plantar aspect of the foot, starting 0.5 cm from the proximal edge of the heel and extending toward the toes. The plantaris muscle was elevated and incised longitudinally. After hemostasis with gentle pressure, the skin was sutured with 5-0 nylon thread. The wound site was covered with a mixture of polymixin B, neomycin, and bacitracin ointment. After surgery, the animals were allowed to recover in their cages.

Spinal Nerve Injury (SNI) Model

The SNI surgery was carried out with minor modification as described in 1. Decosterd, et al., An animal model of persistent peripheral neuropathic pain, Pain, 87 (2000) 149-158. Rats were anesthetized with 2% isoflurane delivered via a nose cone. A 3- to 4-cm skin incision was applied from the left greater trochanter to the knee joint. The muscle layers were separated to expose the sciatic nerve. The trifurcation of the sciatic nerve was identified, and the common peroneal and tibial branches were exposed and ligated with 5-0 silk suture, while special care was taken to avoid damage to the sural nerve. Approximately 2 mm of the nerve segments below the ligature was transected from both the branches.

Peri-Sciatic Nerve Injection

The rats received sciatic nerve block under inhalation anesthesia with isoflurane. Nerve block injections were performed with a 20-gauge needle under isoflurane-oxygen anesthesia as described in J. G. Thalhammer, et al., Neurologic evaluation of the rat during sciatic nerve block with lidocaine, Anesthesiology, 82 (1995) 1013-1025. The needle was introduced posteromedial to the greater trochanter pointing in an anteromedial direction.

The rats were divided into different groups according to the different pain model performed (incisional pain model or SNI model), and were injected with 0.2 mL of a sustained-release ropivacaine hydrochloride PBS solution (SRR or alternatively, PLGA-ROPI) containing 0.25%, 0.125%, and 0.06% of PLGA-ROPI or PLGA-RVC·HCl, a PBS solution containing 0.25% free ropivacaine (FR or alternatively, Free-ROPI), and 2 control solutions of a neat PBS, and a neat PLGA, respectively. The % used here refers to the weight (gram %) of PLGA-ROPI or PLGA-RVC·HCl by the volume (mL) of the solution. For example, 0.25% refers to 0.25 g/100 mL. The animals were divided into 10 groups: incision+0.25% SRR, incision+0.125% SRR, incision+0.06% SRR, incision+0.25% FR, incision+PLGA, incision+PBS. SNI+0.25% SRR, SNI+0.125% SRR, SNI+0.06% SRR, SNI+PBS. Each group contained 8 rats. For the incisional pain model, mechanical and heat allodynia test and motor function test with 1 h intervals were used to examine rats 1 d before surgery and 2 h, 4 h, and consecutively every day post-surgery until 7 d, and then 9 d, 11 d. For the SNI model, mechanical and cold allodynia with 1 h intervals were used to examine rats 1 d before surgery and 7 d post-surgery, post peri-sciatic nerve injection on 7 d post-surgery, and the behavior test was resumed on d8, d10, d12, d14, d16, d19, and d22.

Behavioral Analysis

Mechanical allodynia was tested through measuring paw withdrawal thresholds in response to mechanical stimuli with the up-down testing paradigm as described previously in Y. X. Tao, et al., Impaired neuropathic pain and preserved acute pain in rats overexpressing voltage-gated potassium channel subunit Kv1.2 in primary afferent neurons, Molecular Pain, 10 (2014) 8. The rats were placed in Plexiglas chambers on an elevated mesh screen. Von Frey filaments in log increments of force (0.407, 0.692, 1.202, 2.041, 3.63, 5.495, 8.511, 15.14 g) were applied to the plantar surface of the rats' left and right hind paws. The 2.041-g stimulus was applied first. If a positive response occurred, the next smaller von Frey hair was used; if a negative response was observed, the next larger von Frey hair was used. The test was terminated when (i) a negative response was obtained with the 15.14-g hair or (ii) three stimuli were applied after the first positive response. Paw withdrawal threshold was determined by converting the pattern of positive and negative responses to the von Frey filament stimulation to a 50% threshold value with a formula provided by Dixon as described in S. R. Chaplan, et al., Quantitative assessment of tactile allodynia in the rat paw, Journal of Neuroscience Methods, 53 (1994) 55-63.

Heat allodynia was tested through measuring paw withdrawal latencies to noxious heat with a Model 336 Analgesic Meter (IITC Inc/Life Science Instruments, Woodland Hills. CA, USA) as described previously in Y. X. Tao, et al., Impaired neuropathic pain and preserved acute pain in rats overexpressing voltage-gated potassium channel subunit Kv1.2 in primary afferent neurons, Molecular Pain, 10 (2014) 8. The rats were placed in a Plexiglas chamber on a glass plate. Radiant heat was applied by aiming a beam of light through a hole in the light box through the glass plate to the middle of the plantar surface of each hind paw. When the animal lifted its foot, the light beam was turned off. The length of time between the start of the light beam and the foot lift was defined as the paw withdrawal latency. Each trial was repeated five times at 5-min intervals for each side. A cut-off time of 20 s was used to avoid tissue damage to the hind paw.

Cold allodynia was examined through measuring paw withdrawal latencies to noxious cold (0° C.) with a cold plate, which was set at 0° C. as described previously in Y. X. Tao, et al., Impaired neuropathic pain and preserved acute pain in rats overexpressing voltage-gated potassium channel subunit Kv1.2 in primary afferent neurons, Molecular Pain, 10 (2014) 8. The length of time between the placement of the hind paw on the plate and the animal lifting its hindpaw, with or without paw licking and flinching, was defined as the paw withdrawal latency. Each trial was repeated three times at 10-min intervals for the paw on the ipsilateral side. A cut off time of 60 s was used to avoid paw tissue damage.

Locomotor Function Test

Tests of locomotor function, including placing, grasping and righting reflexes, were performed before and after incision surgery according to the previously described protocol in Y. X. Tao, et al., Impaired neuropathic pain and preserved acute pain in rats overexpressing voltage-gated potassium channel subunit Kv1.2 in primary afferent neurons, Molecular Pain, 10 (2014) 8. (1) Placing reflex: The rat was held with hind limbs slightly lower than the forelimbs and the dorsal surfaces of the hind paws were brought into contact with the edge of a table. Whether the hind paws were placed on the table surface reflexively was recorded; (2) Grasping reflex: The rat was placed on a wire grid and whether the hind paws grasped the wire on contact was recorded; (3) Righting reflex: The rat's back was placed on a flat surface and whether it immediately assumed the normal upright position was recorded.

Scores for placing, grasping, and righting reflexes were based on counts of each normal reflex exhibited in five trials. In addition, the animal's general behaviors, including spontaneous activity (e.g. walking and running), were observed.

Electron Microscopy

The rats were anesthetized with isoflurane and perfused with 300 mL of 2.5% gluteraldehyde in 0.1M sodium cacodylate buffer (pH 7.4). After perfusion, sciatic nerves were dissected, postfixed at 4° C. for 3 hours. After dehydrated by gradient ethanol elution, samples were cleared by propylene, then infiltrated with resin and embed in moulds. Transmission electronic microscopy images were acquired by a Hitachi H-7500 transmission electron microscope (Hitachi, Ltd. Japan).

Immunohistochemistry

Immunohistochemistry analysis were performed as described previously in Y. X. Tao, et al., Nerve injury-induced epigenetic silencing of opioid receptors controlled by DNMT3a in primary afferent neurons, Pain, 158 (2017) 1153-1165. The rats were anesthetized with isoflurane and perfused with 300 mL of 4% paraformaldehyde in 0.1 M phosphate-buffered saline (PBS) (pH 7.4). After perfusion, sciatic nerves were dissected, postfixed at 4° C. for 4 hours and cryoprotected in 30% sucrose overnight. The transverse and longitudinal sections were cut on a cryostat at a thickness of 20 µm. The sections were blocked for 1 hour at 25° C. in 0.01M PBS containing 5% goat serum and 0.3% Triton X-100. Sections were incubated overnight at 4° C. with mouse anti-myelin basic protein (MBP) (1:500; Biolegend, San Diego, CA). The sections were then incubated with a mixture of goat anti-mouse antibody conjugated to Cy2 (1:500; Jackson ImmunoResearch, West Grove, PA) for 2 hours at room temperature. Immunofluorescence-labeled images were generated using a Leica DMI4000 fluorescence microscope with a DFC365FX camera (Leica, Germany).

Histology

The rats were anesthetized with isoflurane and sciatic nerves were harvested and fixed in 4% paraformaldehyde. Following tissue fixation and dehydration, sciatic nerves were embedded in Optimal cutting temperature compound (OCT compound) and 20-µm thin slices were cut on a cryostat, then stained using hematoxylin and eosin stain technique. Nerve structures were observed using a Nikon microscope (Nikon Eclipse 80i, Japan).

Western Blot Analysis

Protein extraction and Western blot analysis were carried out as described in Y. X. Tao, et al., The transcription factor C/EBPbeta in the dorsal root ganglion contributes to peripheral nerve trauma-induced nociceptive hypersensitivity, Sci. Signal, 10 (2017). The bilateral L4/5 spinal cords were harvested. The tissues were homogenized in lysis buffer (10 mM tris, 1 mM phenylmethylsulfonyl fluoride, 5 mM MgCl2, 5 mM EGTA, 1 mM EDTA, 1 mM dithiothreitol, 40 mM leupeptin, 250 mM sucrose). After centrifugation at 4° C. for 15 min at 1000 g, the supernatant was collected for cytosolic proteins, and the pellet was collected for nuclear proteins. The pellet was dissolved in lysis buffer plus 2% SDS and 0.1% Triton X-100 (SDS lysis buffer) and then sonicated on ice. The samples from the cultured neurons were directly dispersed in lysis buffer, centrifuged, and sonicated. After protein concentration was measured, the samples were heated at 99° C. for 5 min and loaded onto a 4 to 15% stacking/7.5% separating SDS-polyacrylamide gel (Bio-Rad Laboratories). The proteins were then electrophoretically transferred onto a polyvinylidene difluoride membrane (Bio-Rad Laboratories). After being blocked with 3% nonfat milk in tris-buffered saline containing 0.1% Tween 20 for 2 hours, the membranes were then incubated at 4° C. overnight with the following antibodies: rabbit anti-phospho-ERK1/2 (Thr202/Tyr204; 1:1000, Cell Signaling Technology), rabbit anti-ERK1/2 (1:1000, Cell Signaling Technology), mouse anti-GFAP (1:1000, Cell Signaling Technology), and rabbit anti-histone H3 (1:1000, Cell Signaling Technology). The proteins were detected by horseradish peroxidase-conjugated anti-rabbit or anti-mouse secondary antibody (1:3000, Bio-Rad Laboratories) and visualized by chemiluminescence reagent (enhanced chemiluminescence, Bio-Rad Laboratories). Images were generated using ChemiDoc XRS System with Image Lab software (Bio-Rad Laboratories). Band intensities were quantified with densitometry by System with Image Lab software (Bio-Rad Laboratories). Band intensities were normalized to GAPDH.

Statistical Analysis

All results were collected randomly and given as means±SEM. The data were statistically analyzed with two-tailed, paired/unpaired Student's t-test and a one-way or two-way ANOVA. When ANOVA showed a significant difference, pairwise comparisons between means were tested by the post hoc Tukey method (SigmaStat, San Jose, CA). Significance was set at p<0.05.

Results

Preparation and Characterization of RVC·HCl Microparticles

In this study, we fabricated the microparticles by double-emulsion solvent evaporation techniques. The hydrophilic RVC·HCl was encapsulated into the PLGA microparticles (FIG. 1A).

From the DLS measurement, the mean diameters of RVC·HCl microparticles were found as 1.7±0.2 μm (FIG. 1B). The zeta potential and PDI was −17.1±2.5 mV and 0.134±0.029, respectively. The EE was 12.67%±0.76% and DLC was 3.62%±0.22% for the RVC·HCl microparticles.

The size distribution and surface morphology of prepared microparticles were examined through SEM images (FIG. 1C). The RVC·HCl microparticles were found to be uniformly spherical, and have smooth surfaces with some deviations and nominal aggregation. These results were in agreement in size with the DLS measurements.

In vitro release profiles of RVC·HCl microparticles were shown in FIG. 1D. 25.6% of the total RVC·HCl was rapidly released over the first 8 h, followed by a sustained release after 12 h. This controlled release of RVC·HCl from the microparticles extended over 6 days, reaching a maximum value of 95.7% thereafter.

Effect of Particle Size on Injectability

The effect of polymer particle size on injectability of the ropivacaine hydrochloride formulation was shown in Table 1:

TABLE 1

Effect of Particle Size on injectability for 25 G Syringes

| Particle Size | Drug Con. | | | | |
|---|---|---|---|---|---|
| | 12 ± 2.4 mg/μl (stock solution) | 5 mg/ml | 2.5 mg/ml | 1.25 mg/ml | 0.6 mg/ml |
| 0 < 2 μm | not injectable | injectable | injectable | injectable | injectable |
| >2 μm | not injectable | not injectable | not injectable | not injectable | injectable |

It was shown that the ropivacaine hydrochloride formulation with particle size larger than 2 μm in diameter was not injectable through 25-gauge syringe when the concentration of the drug-loaded particles reached 1.25 mg/mL (or in the alternatively, 0.125%).

Effect of Peri-Sciatic Nerve Injection on Postsurgical Pain

Figure 2:
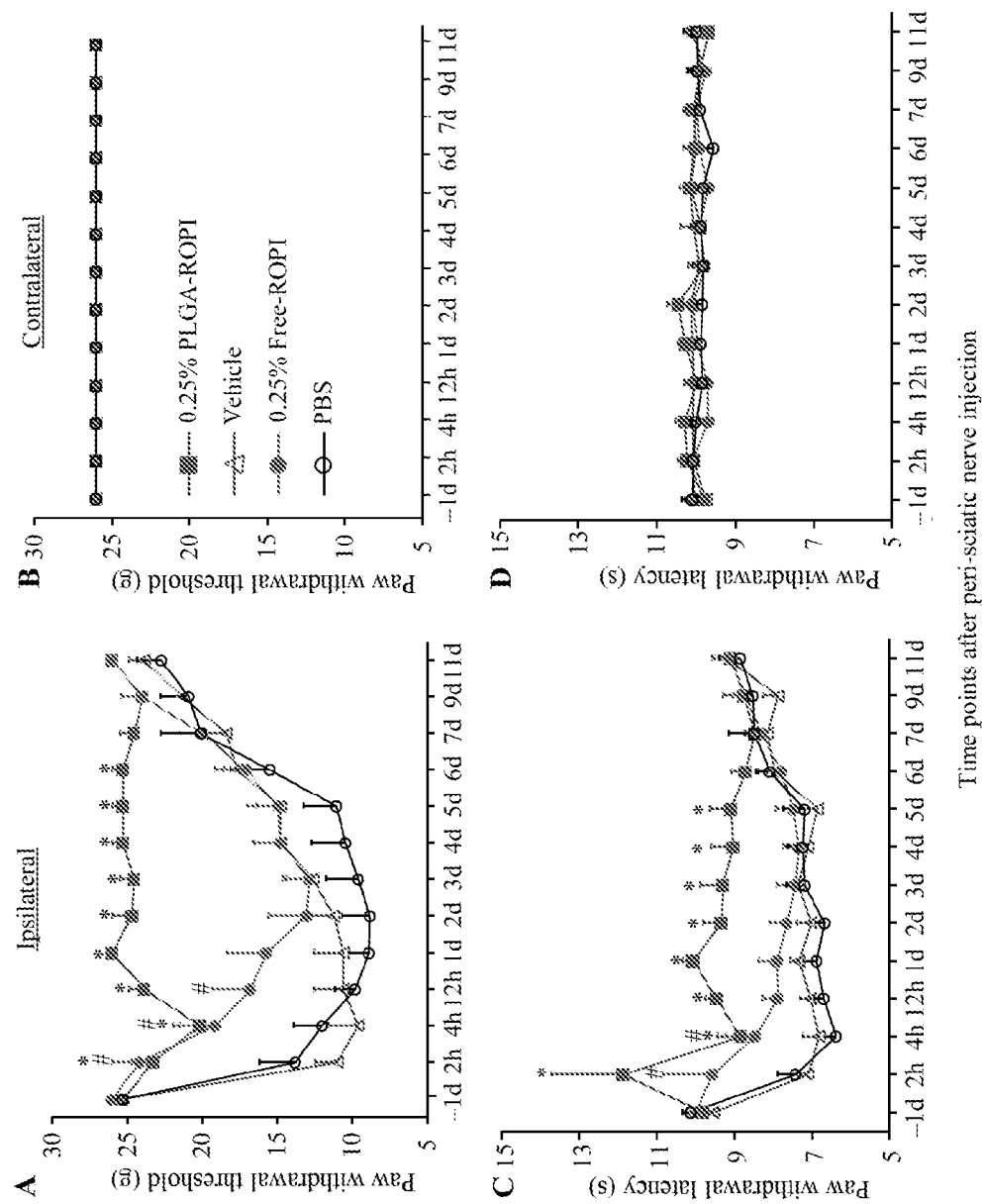
FIG. 2A depicts paw withdrawal thresholds on the ipsilateral side to mechanical stimulation by incision in rats after peri-sciatic nerve injection of 0.25% sustained-release ropivacaine (SRR) (–■–), 0.25% common free ropivacaine (FR) (–●–), PLGA (–▲–), and phosphate buffered saline (PBS) (–⊖–).
FIG. 2B depicts paw withdrawal thresholds on the contralateral side to mechanical stimulation by incision in rats after peri-sciatic nerve injection of 0.25% SRR (–■–), 0.25% FR (–●–), PLGA (–▲–), and PBS (–⊖–).
FIG. 2C depicts paw withdrawal latency on the ipsilateral side to mechanical stimulation by incision in rats after peri-sciatic nerve injection of 0.25% SRR (–■–), 0.25% FR (–●–), PLGA (–▲–), and PBS (–⊖–).
FIG. 2D depicts paw withdrawal thresholds on the contralateral side to mechanical stimulation by incision in rats after peri-sciatic nerve injection of 0.25% SRR (–■–), 0.25% FR (–●–), PLGA (–▲–), and PBS (–⊖–).
Figure 3:
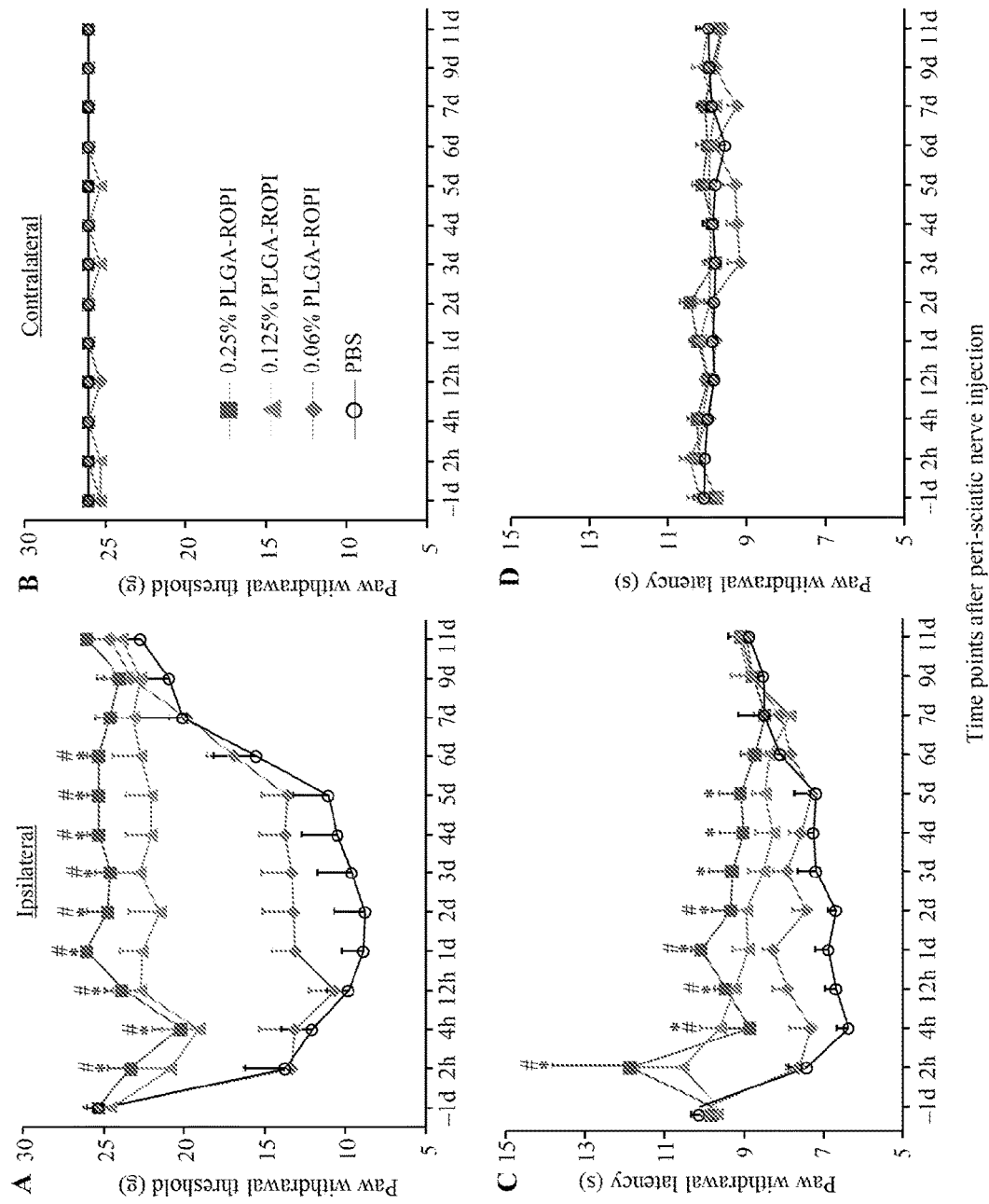
FIG. 3A depicts paw withdrawal thresholds on the ipsilateral side to mechanic stimulation by incision in rats after peri-sciatic nerve injection of 0.25% SRR (–■–), 0.125% SRR (–◆–), 0.06% SRR (–▲–), and PBS (–⊖–).
FIG. 3B depicts paw withdrawal thresholds on the contralateral stimulation by incision in rats after peri-sciatic nerve injection of 0.25% SRR (–■–), 0.125% SRR (–◆–), 0.06% SRR (–▲–), and PBS (–⊖–).
FIG. 3C depicts paw withdrawal latency on the ipsilateral side to mechanical stimulation by incision in rats after peri-sciatic nerve injection of 0.25% SRR (–■–), 0.125% SRR (–◆–), 0.06% SRR (–▲–), and PBS (–⊖–).
FIG. 3D depicts paw withdrawal thresholds on the contralateral side to mechanical stimulation by incision in rats after peri-sciatic nerve injection of 0.25% SRR (–■–), 0.125% SRR (–◆–), 0.06% SRR (–▲–), and PBS (–⊖–).

To examine whether SRR have analgesic effect on postoperative pain when applying on a sciatic nerve, we performed unilateral hindpaw plantar incision in male rats after peri-sciatic nerve injection of SRR in different concentration (0.25%, 0.125%, and 0.06%), 0.25% FR, and PBS and PLGA control solutions. It showed that the incision led to persistent mechanical, thermal pain hypersensitivities on the ipsilateral (but not contralateral) side in the control groups (FIGS. 2 and 3). Pain hypersensitivity reached its peak within the first 24 h after surgery, lasted for 5-6 days, and gradually disappeared starting from day 7 post-surgery. As expected, the injection of PLGA solution alone did not alter paw responses to mechanical or heat stimuli during the observation period, and the common free ropivacaine only has analgesic effect during the first 24 h post injection. With the same dose of SRR (as in the calculation of ropivacaine), an analgesia effect can be observed for continuously 5-6 days post-surgery, while lower doses of SRR can provide a 2-6 days analgesia (0.2 mL solution of 0.125% SRR) or none at all (0.2 mL solution of 0.06% SRR) (FIG. 3). Compared to the control group of incision+PBS, paw withdrawal thresholds to mechanical stimulation of the incision+0.25% SRR group were increased by 69% ($P<0.05$), 68% ($P<0.05$), 143% ($P<0.05$), 193% ($P<0.05$), 181% ($P<0.05$), 155% ($P<0.05$), 142% ($P<0.05$), 128% ($P<0.05$), 63% ($P>0.05$), 22% ($P>0.05$), 15% ($P>0.05$), 14% ($P>0.05$), on time points 2 h, 4 h, 12 h, 1 d, and consecutive every day until 7 d, then 9 d, 11 d after surgery, respectively (FIG. 2A). Additionally, paw withdrawal latencies to heat stimulation of the incision+0.25% SRR group were increased by 60% ($P<0.05$), 39% ($P<0.05$), 41% ($P<0.05$), 47% ($P<0.05$), 40% ($P<0.05$), 29% ($P<0.05$), 24% ($P<0.05$), 26% ($P<0.05$), and 8% ($P>0.05$) on time points 2 h, 4 h, 12 h, 1 d, and consecutive every day until 6 d after surgery, respectively (FIG. 2C). Analgesic effect was completely abolished on day 7 post-surgery in incision+0.25% SRR group. Meanwhile, the incision+0.25% FR group showed increase of paw withdrawal thresholds to mechanical stimulation by 76% ($P<0.05$), 59% ($P<0.05$), 71% ($P<0.05$), as well as of paw withdrawal latencies to heat stimulation by 29% ($P<0.05$), 33% ($P<0.05$), 18% ($P<0.05$) on time points 2 h, 4 h, and 12 h, respectively (FIGS. 2A and 2C), compared to group incision+PBS. There was no significant change in paw withdrawal threshold and latencies between 2 control groups, incision+PBS and incision+PLGA.

The block effect was also dose-dependent. Incision+0.125% SRR group demonstrated much lower increases in paw withdrawal thresholds, which were 51% ($P<0.05$), 59%

(P<0.05), 131% (P<0.05), 154% (P<0.05), 144% (P<0.05), 136% (P<0.05), 110% (P<0.05), 99% (P<0.05), 47% (P>0.05), 15% (P>0.05), 9% (P>0.05), 5% (P>0.05), on time points 2 h, 4 h, 12 h, 1 d, and consecutive every day until 7 d, then 9 d, 11 d after surgery, respectively (FIG. 3A). As for paw withdrawal latencies, incision+0.125% SRR group demonstrated an increase of 42% (P<0.05), 51% (P<0.05), 38% (P<0.05), 29% P<0.05), 34% (P<0.05), 18% (P>0.05), 14% (P>0.05), 18% (P>0.05), and 3% (P>0.05) on time points 2 h, 4 h, 12 h, 1 d, and consecutive every day until 6 d after surgery, respectively (FIG. 3C). There was no significant difference in paw withdrawal threshold and latencies between incision+0.06% SRR and incision+PBS groups.

The results of locomotor function were shown in Table 2:

period, i.e., 10-14 days post-surgery (which was 3-7 days post injection), also the increase of paw withdrawal thresholds and latencies were on much smaller scale. Paw withdrawal thresholds to mechanical stimulation were increased by 334% (P<0.05), 183% (P<0.05), 210% (P<0.05), 229% (P<0.05), 122% (P>0.05), 93% (P>0.05), 89% (P>0.05) on 8 d, 10 d, 12 d, 14 d, 16 d, 19 d, and 22 d post SNI surgery (which was 1 d, 3 d, 5 d, 7 d, 9 d, 12 d, and 15 d after peri-sciatic nerve injection of SRR) compared to the control group SNI+PBS (FIG. 4A). Paw withdrawal latencies to cold stimulation were increased by 77% (P<0.05), 60% (P<0.05), 25% (P>0.05), 26% (P>0.05), 19% (P>0.05), 27% (P>0.05), 4% (P>0.05) on 8 d, 10 d, 12 d, 14 d, 16 d, 19 d, and 22 d post SNI surgery compared to group SNI+PBS

TABLE 2

Animal Motor Function for Microparticle Formulations

| | 2 h | | | 12 h | | | 1 d | | |
|---|---|---|---|---|---|---|---|---|---|
| | Placing reflex | Grasping reflex | Righting reflex | Placing reflex | Grasping reflex | Righting reflex | Placing reflex | Grasping reflex | Righting reflex |
| 0.25% PLGA-ROPI | 5(0) | 3.75(0.82) | 5(0) | 5(0) | 5(0) | 5(0) | 5(0) | 5(0) | 5(0) |
| 0.125% PLGA-ROPI | 5(0) | 3.75(0.82) | 5(0) | 5(0) | 5(0) | 5(0) | 5(0) | 5(0) | 5(0) |
| Vehicle | 5(0) | 5(0) | 5(0) | 5(0) | 5(0) | 5(0) | 5(0) | 5(0) | 5(0) |
| 0.25%-Free-ROPI | 5(0) | 4.38(0.63) | 5(0) | 5(0) | 5(0) | 5(0) | 5(0) | 5(0) | 5(0) |
| PBS | 5(0) | 5(0) | 5(0) | 5(0) | 5(0) | 5(0) | 5(0) | 5(0) | 5(0) |

It was shown that locomotor function was slightly altered in group incision+0.25% SRR, incision+0.125% SRR, and incision+FR during the first 2 h after surgery, but statistics showed no significant difference.

Effect of Peri-Sciatic Nerve Injection on Neuropathic Pain

Figure 4:
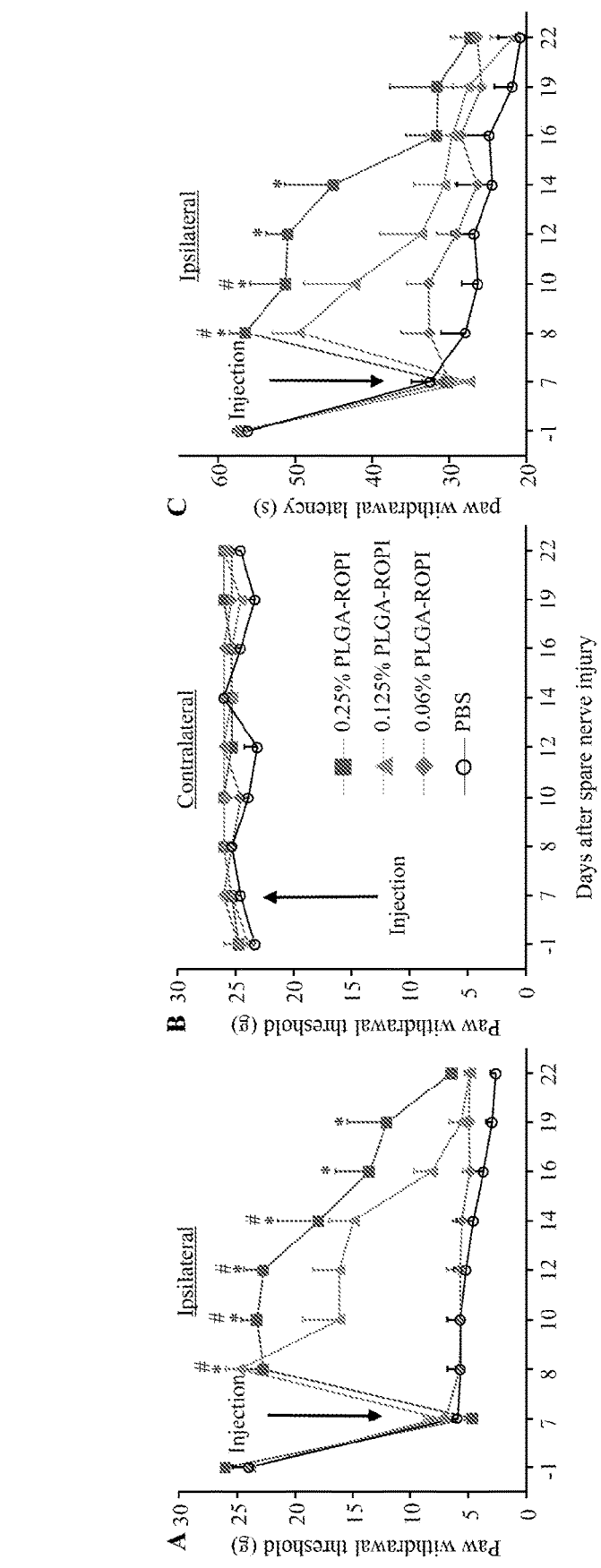
FIG. 4A depicts paw withdrawal thresholds on the ipsilateral side to neuropathic pain by SNI in rats after peri-sciatic nerve injection of 0.25% SRR (–■–), 0.125% SRR (–◆–), 0.06% SRR (–▲–), and PBS (–⊖–).
FIG. 4B depicts paw withdrawal thresholds on the contralateral side to neuropathic pain by SNI in rats after peri-sciatic nerve injection of 0.25% SRR (–■–), 0.125% SRR (–◆–), 0.06% SRR (–◆–), and PBS (–⊖–).
FIG. 4C depicts paw withdrawal latency on the ipsilateral side to neuropathic pain by SNI in rats after peri-sciatic nerve injection of 0.25% SRR (–■–), 0.125% SRR (–◆–), 0.06% SRR (–▲–), and PBS (–⊖–).

We then inquired whether blocking sciatic nerve affects the neuropathic pain produced by SNI. After constructing unilateral SNI model in male rats, we waited for 7 days for neuropathic pain development and stabilization, then performed peri-sciatic nerve injection of SRR in different concentration (0.25%, 0.125%, and 0.06%). It was shown that persistent mechanical and cold allodynia were observed at 7d post-surgery, and maintained for more than 2 weeks until the endpoint of our study. Injection of SRR remarkably alleviated mechanical and thermal pain hypersensitivities for days (FIG. 4). The block effect with group SNI+0.25% SRR lasted for 7-12 days. Paw withdrawal thresholds to mechanical stimulation were increased by 300% (P<0.05), 310% (P<0.05). 337% (P<0.05), 295% (P<0.05), 269% (P<0.05), 314% (P<0.05), 147% (P>0.05) on 8 d, 10 d, 12 d, 14 d, 16 d, 19 d, and 22 d post SNI surgery (which was 1 d, 3 d, 5 d, 7 d, 9 d, 12 d, and 15 d after peri-sciatic nerve injection of SRR) compared to the control group SNI+PBS (FIG. 4A). Paw withdrawal latencies to cold stimulation were increased by 103% (P<0.05), 94% (P<0.05), 90% (P<0.05), 84% (P<0.05), 27% (P>0.05), 44% (P>0.05), 31% (P>0.05) on 8 d, 10 d, 12 d, 14 d, 16 d, 19 d, and 22 d post SNI surgery, respectively (FIG. 4C). Analgesic effect was completely abolished on day 22 post-surgery (15 days after injection) in SNI+0.25% SRR group.

Again, the blockade was dose-dependent. For group SNI+0.125% SRR, the analgesic effect lasted for a much shorter (FIG. 4C). There was no significant difference in paw withdrawal threshold and latencies between SNI+0.06% SRR and SNI+PBS groups.

Figure 5:
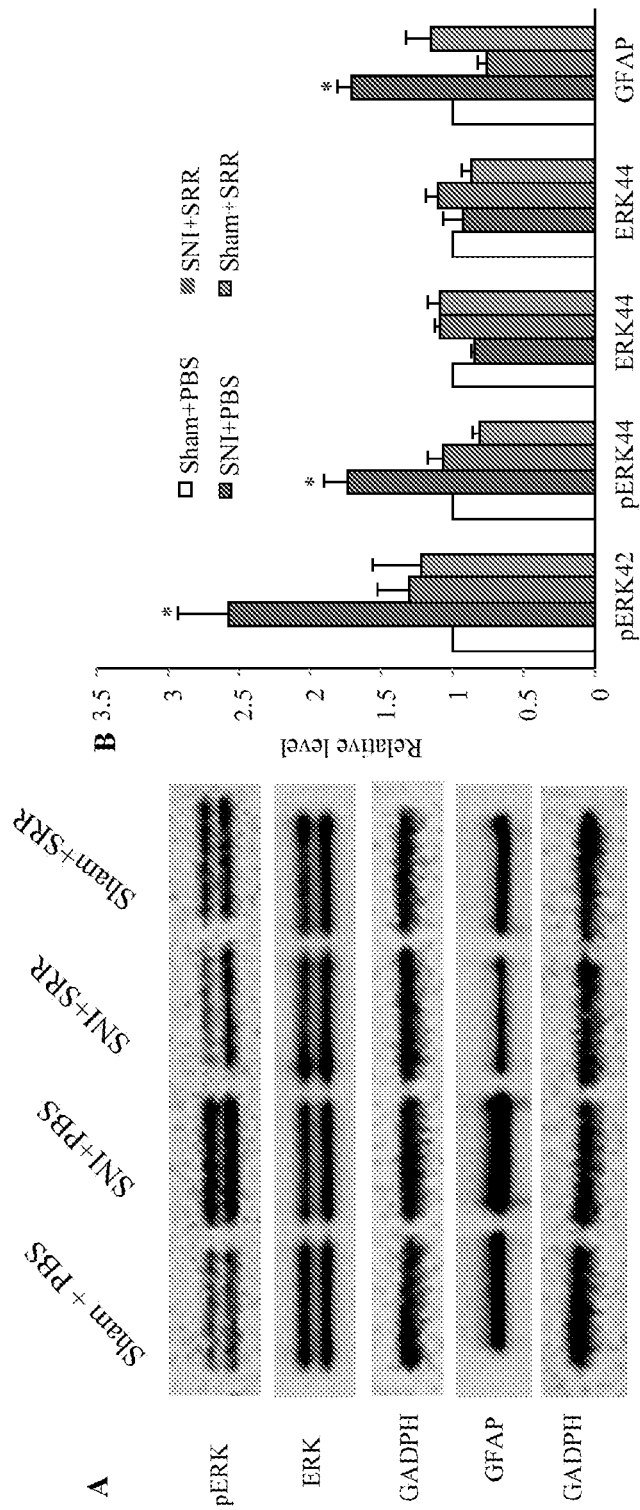
FIG. 5 depicts the effect of 0.25% SRR peri-sciatic nerve injection on spinal nerve injury-induced spinal cord dorsal horn central sensitization as indicated by the increases in the phosphorylation of extracellular signal-regulated kinase 1/2 (pERK1/2) and abundance of glial fibrillary acidic protein (GFAP) in the ipsilateral L4/5 spinal cord dorsal horn on day 7 post-spinal nerve injury (SNI).
Figure 6:
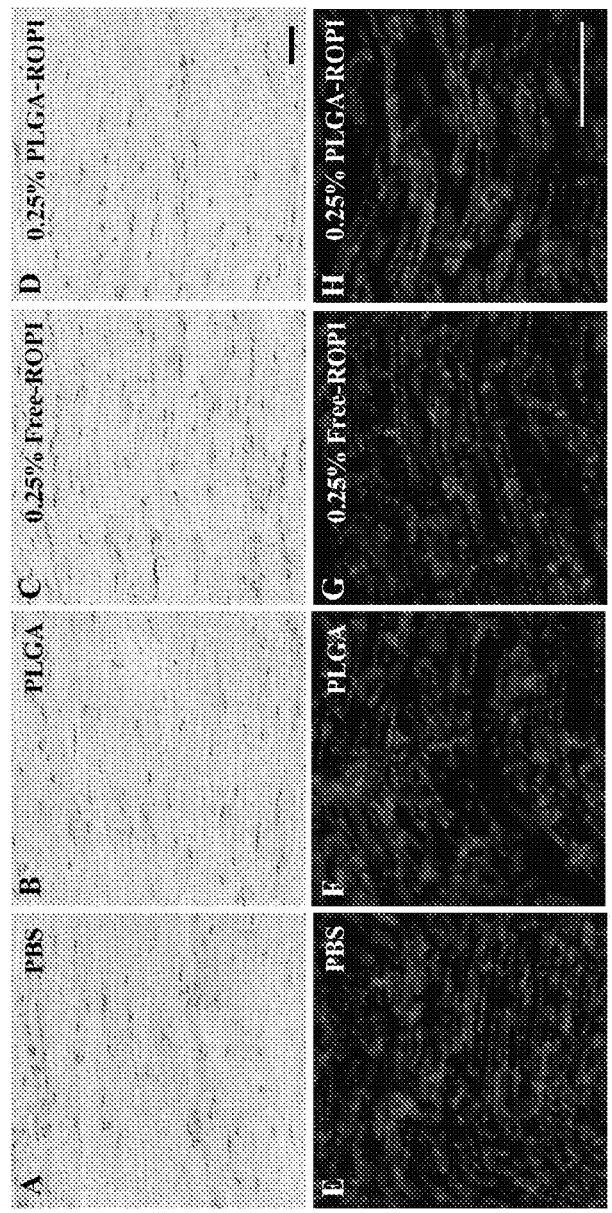
FIGS. 6A-6D depict microscopic examination of sciatic nerve and surrounding tissues 11 days post-injection of PBS, PLGA, 0.25% FR (indicated as 0.25% Free-ROPI), and 0.25% SRR (indicated as 0.25% PLGA-ROPI).
FIGS. 6E-6H depict MBP expression pattern of sciatic nerve 11 days post-injection of PBS. PLGA. 0.25% FR (indicated as 0.25% Free-ROPI), and 0.25% SRR (indicated as 0.25% PLGA-ROPI).

We also examined whether sciatic nerve block affected SNI-induced dorsal horn central sensitization as indicated by increases in the phosphorylation of extracellular signal-regulated kinase 1/2 (ERK1/2) and glial fibrillary acidic protein (GFAP) in the dorsal horn neuropathic pain model as described in Y. X. Tao, et al., Short-Term Sleep Disturbance-Induced Stress Does not Affect Basal Pain Perception, but Does Delay Postsurgical Pain Recovery, J. Pain, 16 (2015) 1186-1199. It was shown that the phosphorylation of ERK1/2 (but not total ERK 1/2) and GFAP was significantly increased in the ipsilateral L4/5 dorsal horn in rats subjected to SNI but not in those that received sham surgery. The injection of 0.25% SRR successfully reversed the increase of phosphorylated ERK1/2 and GFAP by 49% (P<0.05), 38% (P<0.05), 56% (P<0.05), respectively (FIG. 5). The injection of 0.25% SRR significantly reversed the increases in pERK1/2 and GFAP. pERK1/2 (but not total ERK) is a marker for neuronal activation. GFAP is a marker for astrocyte activation. *p<0.05, vs Sham+PBS. N=3/group.

Possible Tissue Reaction and Neurontoxicity of SRR

Rats injected with PBS, PLGA, 0.25% FR (i.e., 0.25% Free ROPI), and 0.25% SRR (i.e., 0.25% PLGA-ROPI) were euthanized 11 days after injection (n=3 for each group), and the sciatic nerve and surrounding tissues were harvested, sectioned for histology, and stained with hematoxylin-eosin (H&E). SRR were not observed on gross dissection. Microscopic examination revealed no significant inflammation in all groups (FIGS. 6A-6D).

To examine whether injection of SRR injured the nerve fiber, we investigated the MBP expression pattern of sciatic nerve on 11 days post injection of PBS, PLGA, 0.25% FR, and 0.25% SRR (n=3 for each group). Among all four groups, MBP was expressed in the same pattern, no abnormality was observed considering myelin morphology (FIGS. 6E-H).

Figure 7:
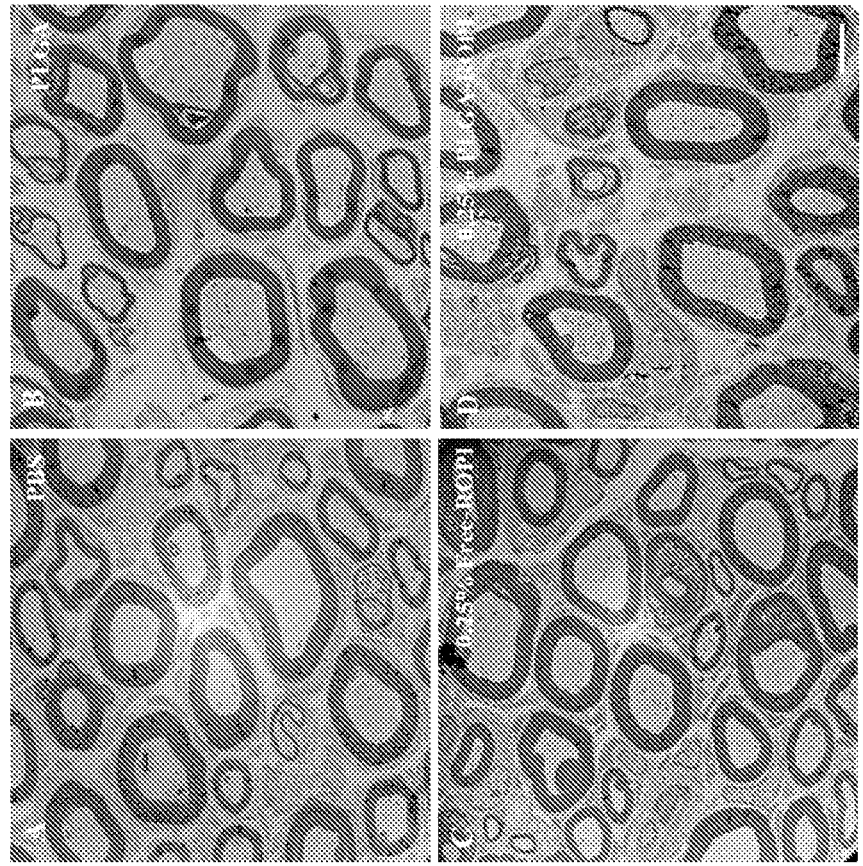
FIGS. 7A-7D depict ultrastructure of sciatic nerve 11 days post-injection of PBS, PLGA, 0.25% FR (indicated as 0.25% Free-ROPI), and 0.25% SRR (indicated as 0.25% PLGA-ROPI).

To observe the ultrastructure of sciatic nerve after injection, we harvested ipsilateral sciatic nerves on day 11 after injection of PBS. PLGA, 0.25% FR, and 0.25% SRR (n=3 for each group), then processed the tissue to be examined under TEM. For each group, myelin sheaths could be seen enveloping nerve fiber, while the sheaths were intact and tightly laminated without any discontinuities. Specific features of the degeneration of myelin sheath including thinner lamellae, loose lamellae, split myelin lamellae with discontinuities, or vacuole-like inclusions in the cytoplasm of Schwann cells were not observed in any of the nerve tissue. Although a very slight separation of myelin sheath layers appeared in a few sections in each group, there was no significant difference among groups (FIG. 7).

The comparative examples were also prepared as follows.
Preparation of RVC·HCl-Loaded PLGA Nanoparticles The nanoparticles (NPs) encapsulated with a payload of ropivacaine were formulated via the double-emulsion solvent evaporation technique. In brief, copolymer PLGA-PEG were dissolved in dichloromethane (DCM). Ropivacaine hydrochloride solution (0.5 mL) was added drop-wise into 1 mL of PLGA-PEG solution and emulsified by probe sonification to form the first emulsion. Next, the emulsified mixture was added into 3 mL of aqueous solution containing 1% poly(vinyl alcohol) (PVA), followed by probe sonification to form the double emulsion. The final emulsion solution was poured into 15 mL of water and stirred for 3 h to allow the DCM solvent to evaporate and the particles to harden. The remaining organic solvent and free molecules were removed by washing the particle solution three times using an Amicon Ultra-4 centrifugal filter (MWCO 100 kDa; Millipore). The NP size and zeta potential were determined by using a ZetaPALS dynamic light-scattering (DLS) detector (15-mW laser, incident beam of 676 nm; Brookhaven Instruments Corporation). The particle size was characterized as 200 nm using DLS.

Peri-Sciatic Nerve Injection

The rats were injected with 0.2 mL of a ropivacaine hydrochloride PBS solution containing 0.25% Nano-ROPI particles prepared above, a PBS solution containing 0.25% free ropivacaine (FR or alternatively, Free-ROPI), and 1 control solution of a neat PBS.

Figure 8:
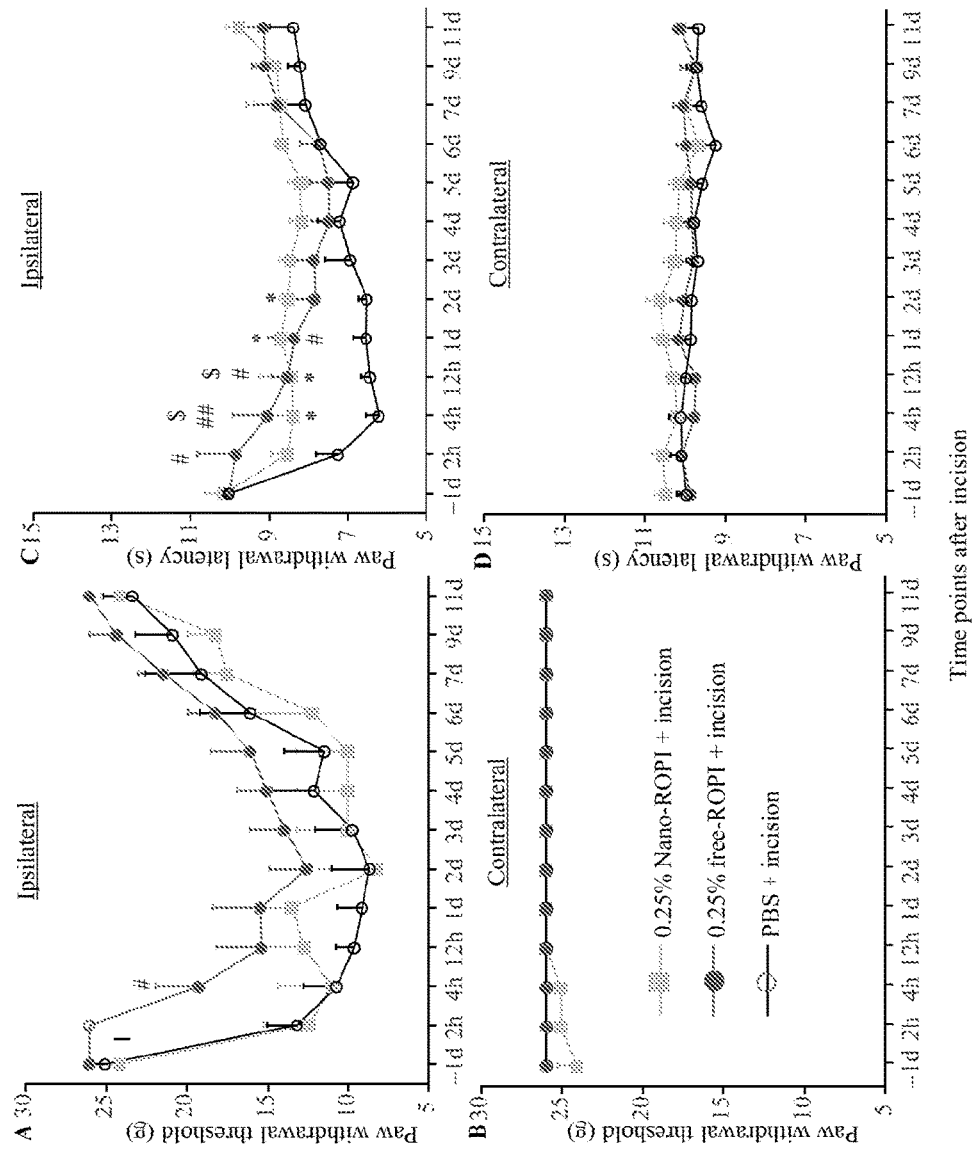
FIG. 8A depicts paw withdrawal thresholds on the ipsilateral side to mechanical stimulation by incision in rats after peri-sciatic nerve injection of 0.25% Nano-ROPI (■), 0.25% FR (●), and PBS (◯).
FIG. 8B depicts paw withdrawal thresholds on the contralateral side to mechanical stimulation by incision in rats after peri-sciatic nerve injection of 0.25% Nano-ROPI (■), 0.25% FR (●), and PBS (◯)
FIG. 8C depicts paw withdrawal latency on the ipsilateral side to mechanical stimulation by incision in rats after peri-sciatic nerve injection of 0.25% Nano-ROPI (■), 0.25% FR (●), and PBS (◯).
FIG. 8D depicts paw withdrawal thresholds on the contralateral side to mechanical stimulation by incision in rats after peri-sciatic nerve injection of 0.25% Nano-ROPI (■), 0.25% FR (●), and PBS (◯).

The effect of peri-sciatic nerve nanoparticle encapsulated ropivacaine injection on postsurgical pain in male rats was shown in FIG. 8. Injection of 0.25% Nano-ROPI did not reduce incision-induced hyperalgesia to mechanical stimulation (FIG. 8A), but reduced hyperalgesia to heat stimuli (FIG. 8C) on the ipsilateral side from 4 hours after injection until 2 days post-surgery compared to the control group. No changes in paw withdrawal responses were seen during the observation period on the contralateral side (FIG. 8B, and FIG. 8D). *$p<0.05$, 0.25% Nano-Ropi vs PBS, #$p<0.05$, 0.25% Free-Ropi vs PBS. N=6/group.

While exemplary embodiments have been described herein, it is expressly noted that these embodiments should not be construed as limiting, but rather that additions and modifications to what is expressly described herein also are included within the scope of the invention. Moreover, it is to be understood that the features of the various embodiments described herein are not mutually exclusive and can exist in various combinations and permutations, even if such combinations or permutations are not made express herein, without departing from the spirit and scope of the invention.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

Exemplary Formulations, Methods and Uses are Set Out in the Following Items:

Item 1. An injectable sustained-release formulation comprises a pharmaceutically effective amount of a local anesthetic encapsulated into a plurality of polymeric particles, wherein each particle has a diameter from 1 μm to 4 μm.

Item 2. The injectable sustained-release formulation of item 1, wherein the plurality of polymeric particles is a biodegradable polymer.

Item 3. The injectable sustained-release formulation of item 2, wherein the biodegradable polymer is poly (lactic acid)(PLA), poly(glycolic acid)(PGA), or poly (lactic-co-glycolic acid)(PLGA).

Item 4. The injectable sustained-release formulation of item 2, wherein the biodegradable polymer is poly (lactic-co-glycolic acid)(PLGA).

Item 5. The injectable sustained-release formulation of item 1, wherein the local anesthetic has a loading of 1% to 90% by weight into the plurality of polymeric particles.

Item 6. The injectable sustained-release formulation of item 1, wherein the local anesthetic has a concentration up to 20 mg/mL.

Item 7. The injectable sustained-release formulation of item 1, wherein the plurality of polymeric particles has a concentration in the injectable sustained-release formulation of 160 to 200 mg/mL.

Item 8. The injectable sustained-release formulation of item 1, further comprising a pharmaceutically acceptable additive.

Item 9. The injectable sustained-release formulation of item 8, wherein the pharmaceutically acceptable additive is selected from the group consisting of epinephrine, clonidine, dexmedetomidine, buprenorphine, dexamethasone, tramadol, sodium bicarbonate, and midazolam.

Item 10. The injectable sustained-release formulation of item 1, wherein each polymeric particle is poly(lactic-co-glycolic acid)(PLGA) and has a diameter from 1 μm to 4 μm, and wherein the local anesthetic has a loading of 1% to 75% by weight into the plurality of polymeric particles.

Item 11. The injectable sustained-release formulation of item 1, wherein each polymeric particle is poly(lactic-co-glycolic acid)(PLGA) and has a diameter from 1 μm to 2 μm, and wherein the local anesthetic has a loading of 5 to 25% by weight into the plurality of polymeric particles.

Item 12. The injectable sustained-release formulation of item 10 or 11, wherein the local anesthetic has a concentration up to 20 mg/mL.

Item 13. The injectable sustained-release formulation of item 1, 10, or 11, wherein the local anesthetic is articaine, bupivacaine, dibucaine, etidocaine, levobupivacaine, lidocaine, mepivacaine, prilocaine, ropivacaine, trimecaine, benzocaine, chloroprocaine, cocaine, cyclomethycaine, dimethocaine, piperocaine, propoxycaine, procaine, proparacaine, or tetracaine, or mixtures thereof, or pharmaceutically acceptable salts thereof.

Item 14. The injectable sustained-release formulation of item 1, 10, or 11, wherein the local anesthetic is ropivacaine.

Item 15. An injectable sustained-release formulation comprises a pharmaceutically effective amount of a local anesthetic encapsulated into a plurality of polymeric particles, wherein the local anesthetic is ropivacaine and has a loading of 5 to 25% by weight into the plurality of polymeric particles, and wherein each polymeric particle is poly(lactic-co-glycolic acid)(PLGA) and has a diameter from 1 µm to 2 µm.

Item 16. A method for providing sustained pain relief at a site in a patient, comprising the step of administering the injectable sustained-release formulation of item 1, 5, 10 or 11.

Item 17. A method for providing sustained pain relief at a site in a patient, comprising the step of administering the injectable sustained-release formulation of item 1, wherein:
1) the local anesthetic has a loading of 1% to 90% by weight into the plurality of polymeric particles; and
2) the local anesthetic is released in a controlled release of 1 to 30 mg of local anesthetic per hour at the release site for a time period ranging from 4 hours to 14 days.

Item 18. The method for providing sustained pain relief at a site in a patient of claim 17, wherein:
1) each polymeric particle is poly(lactic-co-glycolic acid)(PLGA); and
2) the local anesthetic has a concentration up to 20 mg/mL.

Item 19. The method for providing sustained pain relief at a site in a patient of item 17 or 18, wherein the plurality of polymeric particles has a concentration in the injectable sustained-release formulation of 160 to 200 mg/mL.

Item 20. The method for providing sustained pain relief at a site in a patient of item 17 or 18, wherein the local anesthetic has a loading of 1% to 75% by weight into the plurality of polymeric particles.

Item 21. The method for providing sustained pain relief at a site in a patient of item 17 or 18, wherein the local anesthetic has a loading of 5% to 25% by weight into the plurality of polymeric particles and wherein each polymeric particle has a diameter from 1 µm to 2 µm.

Item 22. An injectable sustained-release formulation for use in providing sustained pain relief at a site in a patient, wherein
1) the injectable sustained-release formulation comprises a pharmaceutically effective amount of a local anesthetic encapsulated into a plurality of polymeric particles, wherein each particle has a diameter from 1 µm to 4 µm;
2) the local anesthetic has a loading of 1% to 90% by weight into the plurality of polymeric particles; and
3) the local anesthetic is released in a controlled release of 1 to 30 mg of local anesthetic per hour at the release site for a time period ranging from 4 hours to 14 days.

Item 23. The injectable sustained-release formulation for the use of item 22, wherein:
1) each polymeric particle is poly(lactic-co-glycolic acid)(PLGA); and
2) the local anesthetic has a concentration up to 20 mg/mL.

Item 24. The injectable sustained-release formulation for the use of item 22 or 23, wherein the plurality of polymeric particles has a concentration in the injectable sustained-release formulation of 160 to 200 mg/mL.

Item 25. The injectable sustained-release formulation for the use of item 22 or 23, wherein the local anesthetic has a loading of 1% to 75% by weight into the plurality of polymeric particles.

Item 26. The injectable sustained-release formulation for the use of item 22 or 23, wherein the local anesthetic has a loading of 5% to 25% by weight into the plurality of polymeric particles and wherein each polymeric particle has a diameter from 1 µm to 2 µm.

The invention claimed is:

1. An injectable sustained-release formulation suitable for treatment of pathological pain, comprising a pharmaceutically effective amount of a local anesthetic encapsulated into a plurality of polymeric particles, wherein each particle has a diameter from 1 µm to 2 µm, wherein the local anesthetic has a concentration of from 1.25 mg/mL to 20 mg/mL, wherein the plurality of polymeric particles is a biodegradable polymer, and the biodegradable polymer is poly(lactic acid)(PLA), poly(glycolic acid)(PGA), or poly(lactic-co-glycolic acid)(PLGA) and wherein the formulation is injectable with a 25-gauge needle.

2. The injectable sustained-release formulation of claim 1, wherein the biodegradable polymer is poly(lactic-co-glycolic acid)(PLGA).

3. The injectable sustained-release formulation of claim 1, wherein the local anesthetic has a loading of 1% to 90% by weight into the plurality of polymeric particles.

4. The injectable sustained-release formulation of claim 1, wherein the plurality of polymeric particles has a concentration in the injectable sustained-release formulation of 160 to 200 mg/mL.

5. The injectable sustained-release formulation of claim 1, further comprising a pharmaceutically acceptable additive.

6. The injectable sustained-release formulation of claim 5, wherein the pharmaceutically acceptable additive is selected from the group consisting of epinephrine, clonidine, dexmedetomidine, buprenorphine, dexamethasone, tramadol, sodium bicarbonate, and midazolam.

7. The injectable sustained-release formulation of claim 1, wherein each polymeric particle is poly(lactic-co-glycolic acid)(PLGA), and wherein the local anesthetic has a loading of 1% to 75% by weight into the plurality of polymeric particles.

8. The injectable sustained-release formulation of claim 1, wherein each polymeric particle is poly(lactic-co-glycolic acid)(PLGA), and wherein the local anesthetic has a loading of 5% to 25% by weight into the plurality of polymeric particles.

9. The injectable sustained-release formulation of claim 1, wherein the local anesthetic is articaine, bupivacaine, dibucaine, etidocaine, levobupivacaine, lidocaine, mepivacaine, prilocaine, ropivacaine, trimecaine, benzocaine, chloroprocaine, cocaine, cyclomethycaine, dimethocaine, piperocaine, propoxycaine, procaine, proparacaine, or tetracaine, or mixtures thereof, or pharmaceutically acceptable salts thereof.

10. The injectable sustained-release formulation of claim 1, wherein the local anesthetic is ropivacaine.

11. An injectable sustained-release formulation suitable for treatment of pathological pain, comprising a pharmaceutically effective amount of a local anesthetic encapsulated into a plurality of polymeric particles, wherein the local anesthetic is ropivacaine and has a loading of 5% to 25% by weight into the plurality of polymeric particles, and wherein each polymeric particle is poly(lactic-co-glycolic acid) (PLGA) and has a diameter from 1 μm to 2 μm, and wherein the formulation is injectable with a 25-gauge needle and the local anesthetic has a concentration of from 1.25 mg/mL to 20 mg/mL.

12. A method for providing sustained pain relief at a site in a patient, comprising the step of administering the injectable sustained-release formulation of claim 1 to the patient.

13. The method of claim 12, wherein:
1) The local anesthetic has a loading of 1% to 90% by weight into the plurality of polymeric particles; and
2) the local anesthetic is released in a controlled release of 1 to 30 mg of local anesthetic per hour at the release site for a time period ranging from 4 hours to 14 days.

14. The method for providing sustained pain relief at a site in a patient of claim 13, wherein:
each polymeric particle is poly(lactic-co-glycolic acid) (PLGA).

15. The method for providing sustained pain relief at a site in a patient of claim 13, wherein the plurality of polymeric particles has a concentration in the injectable sustained-release formulation of 160 to 200 mg/mL.

16. The method for providing sustained pain relief at a site in a patient of claim 13, wherein the local anesthetic has a loading of 1% to 75% by weight into the plurality of polymeric particles.

17. The method for providing sustained pain relief at a site in a patient of claim 13, wherein the local anesthetic has a loading of 5% to 25% by weight into the plurality of polymeric particles.

18. The injectable sustained-release formulation of claim 1, wherein the plurality of polymeric particles are produced via a solvent evaporation technique using a water-in-oil-in-water double emulsion in which (i) a polymeric material is dissolved in dichloromethane to form a polymer solution, (ii) a solution comprising the local anesthetic, polyvinyl alcohol, and water is mixed with the polymer solution to form a first emulsion, and (iii) the first emulsion is added to a polyvinyl alcohol solution to form the water-in-oil-in-water double emulsion, and
wherein the encapsulation efficiency of the polymeric particles is at least 80%.

19. The injectable sustained-release formulation of claim 11, wherein the plurality of polymeric particles are produced via a solvent evaporation technique using a water-in-oil-in-water double emulsion in which (i) a polymeric material is dissolved in dichloromethane to form a polymer solution, (ii) a solution comprising ropivacaine, polyvinyl alcohol, and water is mixed with the polymer solution to form a first emulsion, and (iii) the first emulsion is added to a polyvinyl alcohol solution to form the water-in-oil-in-water double emulsion, and
wherein the encapsulation efficiency of the polymeric particles is at least 80%.

* * * * *